US009820812B2

(12) United States Patent
Kindermann et al.

(10) Patent No.: US 9,820,812 B2
(45) Date of Patent: Nov. 21, 2017

(54) ELECTROMAGNETIC SKIN TREATMENT DEVICE

(71) Applicant: KONINKLIJKE PHILIPS N.V., Eindhoven (NL)

(72) Inventors: Sebastian Alexander Kindermann, Eindhoven (NL); Marcel Sladecek, Eindhoven (NL); Christian Mikula, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/437,202

(22) PCT Filed: Oct. 22, 2013

(86) PCT No.: PCT/IB2013/059537
§ 371 (c)(1),
(2) Date: Apr. 21, 2015

(87) PCT Pub. No.: WO2014/064608
PCT Pub. Date: May 1, 2014

(65) Prior Publication Data
US 2015/0282878 A1 Oct. 8, 2015

Related U.S. Application Data

(60) Provisional application No. 61/716,661, filed on Oct. 22, 2012.

(51) Int. Cl.
*A61B 18/18* (2006.01)
*A61N 5/00* (2006.01)
(Continued)

(52) U.S. Cl.
CPC .... *A61B 18/18* (2013.01); *A61B 2018/00023* (2013.01); *A61B 2018/0047* (2013.01);
(Continued)

(58) Field of Classification Search
CPC ....... A61N 5/06–2005/073; A61F 7/00; H01H 9/04; A61B 5/00; A61B 18/18; A61B 18/20–18/28
(Continued)

(56) References Cited

U.S. PATENT DOCUMENTS 5,560,362 A * 10/1996 Sliwa, Jr. ............... A61B 8/546
600/439
5,849,029 A * 12/1998 Eckhouse ............ A61B 18/203
607/104
(Continued)

FOREIGN PATENT DOCUMENTS

DE 3107646 A1 10/1982
EP 0885629 A2 12/1998
(Continued)

OTHER PUBLICATIONS

Tria, "Tria Hair Removal LAser Getting Started", 2011, pp. 4-12.*

*Primary Examiner* — Christopher A Flory
*Assistant Examiner* — Jonathan Kuo (57) ABSTRACT

A hand-held skin treatment device comprises a source of electromagnetic radiation, an energy supply electrically coupled to the source and a controller arranged to control the energy supplied to the source of electromagnetic radiation. The source, the energy supply and the controller are enclosed in a watertight housing allowing use of the hand-held skin treatment device in a wet environment. To provide sufficient cooling of the source, the device comprises an internal heat exchanger in heat conducting relation with the source, an external heat exchanger outside of the watertight housing, and a heat path from the internal heat exchanger to the external heat exchanger that passes hermetically through a wall of the watertight housing. With this device, users can conveniently integrate their skin treatment activities with the (Continued)

daily washing routine in a shower or bath. The device is especially useful in the context of hair removal.

14 Claims, 9 Drawing Sheets

(51) Int. Cl.
*A61N 5/06* (2006.01)
*A61B 18/00* (2006.01)

(52) U.S. Cl.
CPC ........... *A61B 2018/00047* (2013.01); *A61B 2018/1807* (2013.01); *A61N 2005/005* (2013.01); *A61N 2005/0644* (2013.01); *F04C 2270/0421* (2013.01)

(58) Field of Classification Search
USPC ........... 600/306; 607/104, 88–94; 606/2–19; 200/302.1, 302.3
See application file for complete search history.

(56) References Cited

U.S. PATENT DOCUMENTS

| | | | | |
|---|---|---|---|---|
| 6,963,039 B1* | 11/2005 | Weng | ............. | H01H 23/06 200/302.1 |
| 7,578,604 B2 | 8/2009 | Lee | | |
| 2004/0147984 A1 | 7/2004 | Altshuler | | |
| 2004/0176754 A1* | 9/2004 | Island | ............. | A61B 18/203 606/9 |
| 2006/0271024 A1* | 11/2006 | Gertner | ............. | A61N 5/0603 606/2 |
| 2007/0038206 A1* | 2/2007 | Altshuler | ............. | A46B 15/0036 606/20 |
| 2007/0106344 A1* | 5/2007 | Darley | ............. | A61N 1/36032 607/55 |
| 2007/0198004 A1 | 8/2007 | Altshuler | | |
| 2008/0139901 A1* | 6/2008 | Altshuler | ............. | A45D 26/0061 600/306 |
| 2009/0240243 A1* | 9/2009 | Brottier | ............. | A45D 26/0004 606/9 |
| 2011/0106067 A1* | 5/2011 | Geva | ............. | A45D 34/042 606/9 |

FOREIGN PATENT DOCUMENTS

| | | | | |
|---|---|---|---|---|
| EP | 1666016 A1 | 6/2006 | | |
| KR | 100801376 B1 | 1/2008 | | |
| KR | 20100002714 A | 1/2010 | | |
| WO | 2004047921 A1 | 6/2004 | | |
| WO | 2007124562 A1 | 11/2007 | | |
| WO | 2008012519 A1 | 1/2008 | | |
| WO | 2009090632 A2 | 7/2009 | | |
| WO | WO 2009090632 A2 * | 7/2009 | ............. | A45D 26/00 |
| WO | 2009109885 A2 | 9/2009 | | |
| WO | 2011067761 A1 | 6/2011 | | |

* cited by examiner

ELECTROMAGNETIC SKIN TREATMENT DEVICE

This application is the U.S. National Phase application under 35 U.S.C. §371 of International Application No. PCT/IB2013/059537, filed on Oct. 22, 2013, which claims the benefit of U.S. Provisional Application No. 61/716,661 filed on Oct. 22, 2012. These applications are hereby incorporated by reference herein.

BACKGROUND OF THE INVENTION

Field of the Invention

The present invention relates to skin treatment devices for application of electromagnetic radiation to the skin, and in particular to hand-held devices that can be used in a wet environment. The invention is for example applicable for removal of hair by application of localised energy to destroy or damage the hair follicle or root, thereby preventing re-growth.

Description of the Related Art

Light-based skin treatment devices are increasingly used for various forms of personal care and therapeutic treatments. Such treatments can include hair removal, skin rejuvenation, acne treatment, pigmentation removal and the like. In addition to treatment in the visible spectrum, other regions of the electromagnetic spectrum are also used, including the infra-red, ultraviolet and radio frequencies. Hereinafter, reference to light is not intended to be limited to the visible spectrum unless otherwise specified.

Hair removal is of particular importance in the context of personal care for both men and women. Removal can take place temporarily by shaving, epilating and waxing, or more permanently by high energy techniques such as laser removal and the use of intense pulsed light (IPL) flash lamps. High energy techniques are frequently used by professional cosmetic technicians in dedicated salons. The devices are relatively complex, and care and experience may be required to avoid injury to a patient. One device is known from US 2008/139901 which describes a photo-cosmetic device usable for various treatments. The device includes a base station and a handpiece coupled by a cable. The handpiece includes a treatment head and a source of electromagnetic radiation and can be provided with active or passive cooling to prevent damage to the head or to the patient's skin.

Recent devices have also been developed for personal use. Such devices are often simpler than professional quality models and may operate at lower power levels and/or may have a smaller treatment head. Nevertheless, they can be effective in temporarily or even permanently removing hair if used over a period of time. A device of this type has been described in WO2004/047921, which includes a hand-held housing incorporating a radiation source and a radiation filter. The radiation filter is designed to adsorb harmful wavelengths of radiation and allow those wavelengths to reach the skin that are required to perform the desired treatment. Due to the significant energy density of the radiation, the filter can become extremely hot. A cooling system is provided in order to avoid overheating.

Although the above mentioned devices have made such forms of light-based skin treatment accessible for the non-professional consumer, the mode of use of these devices remains limited. Consumers increasingly wish to perform grooming and skin-care activities while bathing or showering, but the existing hand-held devices are unsuitable for use in a wet environment and could not be used underwater without damage to the device or danger to the individual. It would therefore be desirable to provide an improved device which increases the flexibility of use and which better enables a user to safely integrate hair removal activities into their lifestyle. At the same time, the improved device should provide sufficient cooling of the source of electromagnetic radiation arranged in the housing of the device. The same applies to other personal skin-care treatments such as skin rejuvenation, wrinkle treatment and the like.

BRIEF SUMMARY OF THE INVENTION

According to the invention, there is provided a hand-held electromagnetic skin treatment device comprising a source of electromagnetic radiation, an energy supply electrically coupled to the source, and a controller arranged to control a supply of energy from the energy supply to the source of electromagnetic radiation. The source, the energy supply and the controller are enclosed in a watertight housing allowing use of the hand-held electromagnetic skin treatment device in a wet environment. The device comprises an internal heat exchanger in heat conducting relation with the source, an external heat exchanger outside of the watertight housing, and a heat path from the internal heat exchanger to the external heat exchanger that passes hermetically through a wall of the watertight housing. In this manner, users can conveniently integrate their hair removal or skin treatment activities with the daily washing routine in a shower or bath. Use on wet skin or in combination with water is not believed to affect the efficiency of hair removal. Water has generally a low absorbency for the wavelength range of around 570 nm to 1000 nm frequently used for hair removal and can even help as a filter to limit radiation that is damaging to the skin. The same applies to other treatments in this frequency range and also to skin rejuvenation treatment in the radio frequency range.

The internal heat exchanger in heat conducting relation with the source, the external heat exchanger outside of the watertight housing, and the heat path from the internal heat exchanger to the external heat exchanger passing hermetically through a wall of the watertight housing jointly provide sufficient cooling of the source of electromagnetic radiation arranged in the watertight housing. Surrounding water can for example be used to cool the source, by interaction with the external heat exchanger, more efficiently than cooling it with an internal air flow as is usual with known devices. Cooling by an internal air flow would not be possible in the case of a watertight housing enclosing the source of electromagnetic radiation. For systems operating with intermittent discharge, such as IPL devices, the time between flashes of the flash lamp can thus be reduced, which leads to less application time and a more efficient procedure.

Conventional consumer IPL devices are recommended to be used according to a prescribed treatment regime, for example every second week for the first five weeks after starting with IPL and every 4-6 weeks after that. Making a hand-held electromagnetic skin treatment device watertight and optimizing it for use in the shower and bath tub opens new opportunities for the whole application procedure. As the shower routine may be carried out a couple of times per week and the skin treatment, for example hair removal, has to be done only 1-2 times per month, it would be possible to treat only a small part of the body during each shower session and thus progressively cover all areas of the body where the hairs have to be removed. The user thus has the freedom to integrate the device into his or her individual beauty routine, in particular since the device can be used under dry conditions, in the bath tub, the whirlpool or under the shower. Similar advantages are encountered for other skin treatments.

Due to the nature of such treatments, considerable heat is generated by the source of electromagnetic radiation and must be dissipated by heat exchange with the environment. The internal and the external heat exchanger may take various forms but should at least be capable of transferring heat from the interior of the watertight housing where the source is located to an exterior location within the wet environment. A number of alternatives are described in detail below, but it is understood that these are not to be construed in a limiting manner.

A still further advantage is that, after a flash of light, fresh water will run over the exposed skin area and cool it immediately, thus reducing pain and skin irritations. Users are already very familiar with shaving and epilating in a wet environment and experience running water as soothing and a pleasant part of what may otherwise be a painful or tedious activity. The present device enhances this experience for skin treatments based on electromagnetic radiation.

In one embodiment, the heat path comprises a cooling fluid circuit at least partially within the watertight housing. In this context, cooling fluid circuit is to be understood to mean a closed circuit through which a cooling fluid may circulate without direct contact with the environmental water. A pump may be provided for circulating the fluid or the flow may be natural e.g. by convection. Intermediate heat exchangers may be provided between the cooling fluid circuit and the source and between the cooling fluid circuit and the environment, depending on the requirements.

Preferably, the internal heat exchanger comprises a heat sink and the external heat exchanger comprises cooling fins. The heat sink and the cooling fins may be integrally formed as a single piece of material, e.g. a metal having good conduction properties. In another embodiment, the heat path comprises one or more heat pipes. These may be filled with an appropriate fluid medium suited to the temperature range encountered by the device. Alternatively or additionally, the heat path may include a thermo-electric element, such as a Peltier element, in order to further enhance heat transfer from the source to the external heat exchanger.

In another embodiment, the device comprises an additional housing portion with passages through which water from an environment may flow without entering an interior of the watertight housing, wherein the external heat exchanger is located at least partially in the additional housing portion. The additional housing portion may form a cooling compartment connected to the watertight housing.

In one particular embodiment, the watertight housing forms part of a shower head connectable to a water supply, wherein the external heat exchanger is located within an interior of the shower head such that the water supplied can flow over the external heat exchanger. The source of electromagnetic radiation may be located in a central region of the shower head, e.g. on a face from which water exits the head. In a shower head embodiment, it may be desirable to have a replaceable module containing at least the energy supply, such that this can be recharged without removal of the complete shower head.

Another alternative embodiment may be embodied as part of a washing glove or scrubbing sponge, wherein the external heat exchanger is located within an interior of the glove or sponge such that it is contacted by water but is not in contact with a hand of the user during normal use. Also, in such an embodiment, it may be desirable to have a modular structure such that the sponge or glove can be separated from other parts of the device for cleaning or disposal.

The device may also be integrated with other skin treatment devices, in particular mechanical hair removal devices such as a shaver or epilator. Light-based hair removal treatments generally still require mechanical removal of the hair above the skin before such treatments. By combining a light-based hair removal device with a wet epilator or shaver, both activities can be performed together and the debris washed away.

Preferably, the watertight housing comprises a faceplate for engaging a user's skin during use, the faceplate having a window allowing irradiation of the skin through the window. The device may further comprise safety detectors disposed around a circumference of the window, e.g. on or close to the faceplate. These safety detectors may be embodied as proximity sensors in order to determine whether the faceplate is in contact with a surface such as the user's skin. In this way, accidental exposure of the user's eyes to light from the source can be avoided. The safety detectors are preferably also watertight. This may be achieved by providing a covering membrane that is welded to or integrally formed with the watertight housing, in particular the faceplate. Various forms of safety detectors may be used. In one embodiment, the safety detectors comprise mechanical microswitches having actuator rods protruding through openings in the face plate, said openings being covered by watertight flexible membranes. In another embodiment, the safety detectors comprise capacitive sensors, each sensor being associated with a blind hole in the faceplate and being arranged to measure a change in capacitance due to skin doming into the blind hole on the application of a pressure, wherein a watertight sealing element is present between each capacitive sensor and the associated blind hole.

The invention is intended to cover all forms of high-energy skin treatment devices based on electromagnetic radiation. This may include e.g. radio-wave radiation. The invention is particularly adapted for skin treatment devices that use light, including laser light and intense pulsed light (IPL). The source of electromagnetic radiation may be considered to be any source capable of generating appropriate energy for the intended skin treatment and may include incandescent light sources, gas discharge light sources and solid state light sources such as LEDs and laser diodes. Preferably, the source has an output of at least 2 J/cm2 during a 0-10 ms pulse. In a further preferred form, the duration of the pulse is between 1 and 100 ms, preferably between 1 and 30 ms.

In one particular embodiment, the device is intended for IPL hair removal. In this case the source should emit sufficient energy to cause at least temporary or semi-permanent damage to the hair root. Most preferably, the source of electromagnetic radiation comprises a flash lamp such as a Xenon lamp, and the controller operates the device as an IPL device. Operation of IPL devices is believed to be otherwise conventional and does not require further explanation here. Nevertheless, in the present context, it is understood that an intense pulsed delivery of light is required, for example with the energy density indicated above. Most preferably, the source emits light in the 560 nm to 1000 nm range over either a broad bandwidth or a narrow bandwidth.

Various forms of controller may be used to control the supply of energy to the source. This may include high-power electronics such as a step-up convertor or a typical laser diode driving unit. According to a preferential form of the invention, the device further comprises a capacitor arranged to be repeatedly charged from the energy supply and repeatedly discharged through the source of electromagnetic radiation. Appropriate power electronics may be provided to control this operation. Preferably, the energy supply comprises a rechargeable battery. It is nevertheless the case that in certain embodiments the battery may be omitted and a capacitor may be charged up sufficiently to perform the treatment during a number of discharge flashes.

The term watertight housing is intended to cover a single housing or a plurality of housings or watertight compartments, to the extent that these allow the device to operate effectively underwater or in a wet environment. In this context, it is evidently understood that the device need at least be waterproof to the extent necessary for use in a bath. In a preferred embodiment, the source, the energy supply and the controller are all contained in a single watertight housing compartment.

In a further preferred embodiment, the housing may comprise one or more impermeable flexible inner liners. These may hermetically enclose the sensitive electronic components in order to provide additional protection against water, e.g. in the event that the watertight housing itself becomes cracked. The watertight housing may be made from plastic material and may be subject to impact as a result of, for example, dropping to a tiled floor or the like. An impermeable flexible inner liner may ensure that the essential electronics remain protected against the impact of water. Additionally or alternatively, the watertight housing may be made with regions of resilient material in order to cushion likely shocks.

The device is preferably provided in combination with a charging station. Such a charging station may comprise a cradle in which the device can be placed and a charging circuit arranged to supply electricity to the energy supply when the device is placed on the cradle. Although generally the whole device will be placed on the charging station, it is understood, as described elsewhere, that just a part of the device could be recharged and then joined to the remainder of the device as a modular assembly.

The invention furthermore relates to the use of the above device for skin treatment in a wet environment, for example to the use for hair removal.

BRIEF DESCRIPTION OF THE DRAWINGS

Features and advantages of the invention will be explained with reference to the following drawings of a number of exemplary embodiments, in which.

DESCRIPTION OF ILLUSTRATIVE EMBODIMENTS

Figure 1:
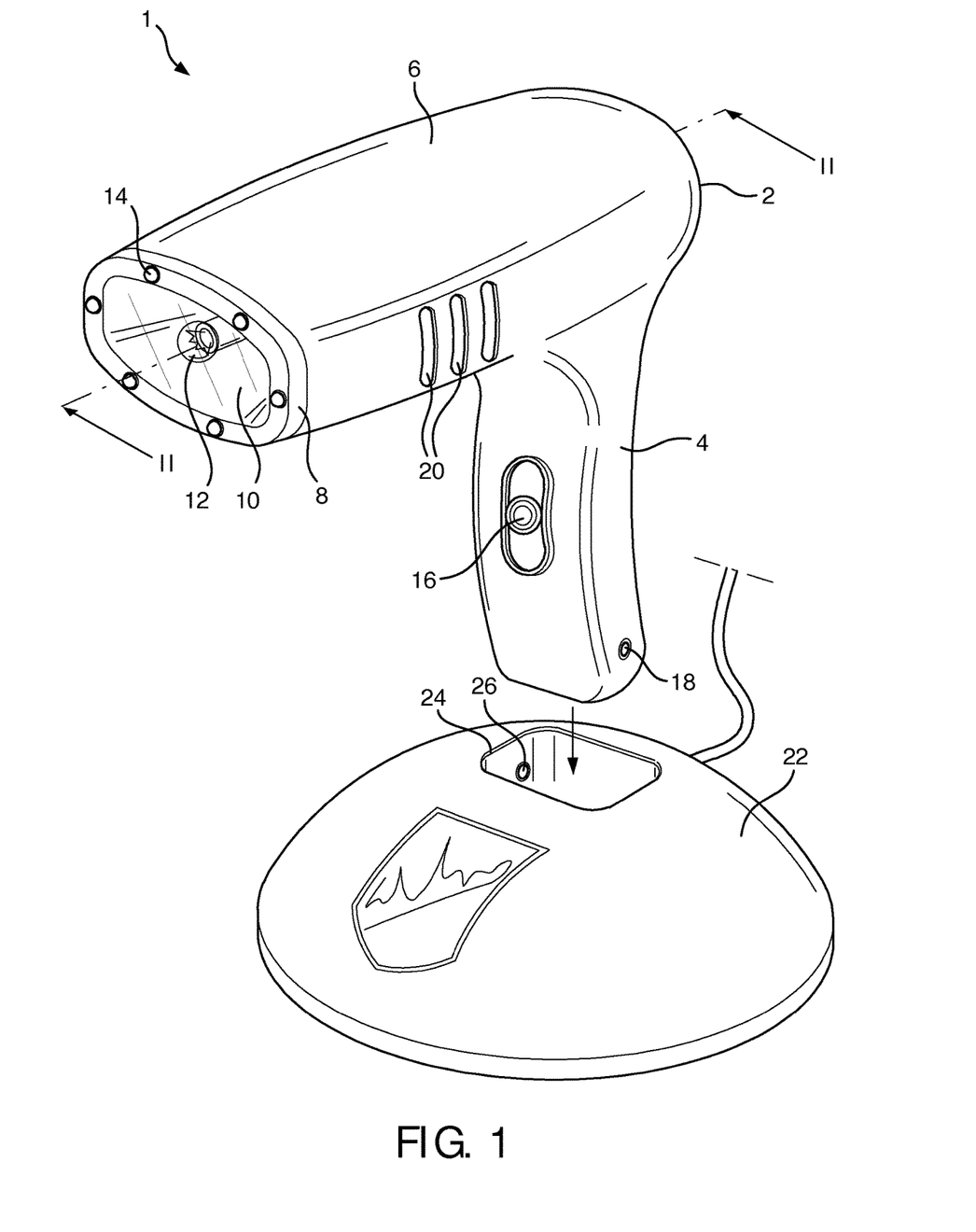
FIG. 1 shows a perspective view of a first embodiment of the present invention.

FIG. 1 shows a perspective view of an IPL hair removal device 1 according to a first embodiment of the invention. Although the invention is further described only in the context of hair removal, it will be understood that it is equally applicable to other skin treatments. The device 1 comprises a watertight housing 2 having a handle portion 4 and a body portion 6. The body portion 6 terminates at a face plate 8 having a transparent window 10, behind which a xenon flash-lamp 12 is located. Safety detectors 14 are distributed around a circumference of the window 10, the purpose of which will be described hereinbelow. The handle portion 4 includes a trigger-like actuation switch 16 and electrical contacts 18, one of which is shown, for electrical recharging of the device. Passages 20 are formed in the body portion 6. Also shown in FIG. 1 is a charging station 22 by means of which the device 1 can be electrically recharged. The charging station 22 has a cradle 24 into which the handle portion 4 can be placed, said cradle having charging terminals 26 that are in alignment and in engagement with contacts 18 on the handle portion 4.

Figure 2:
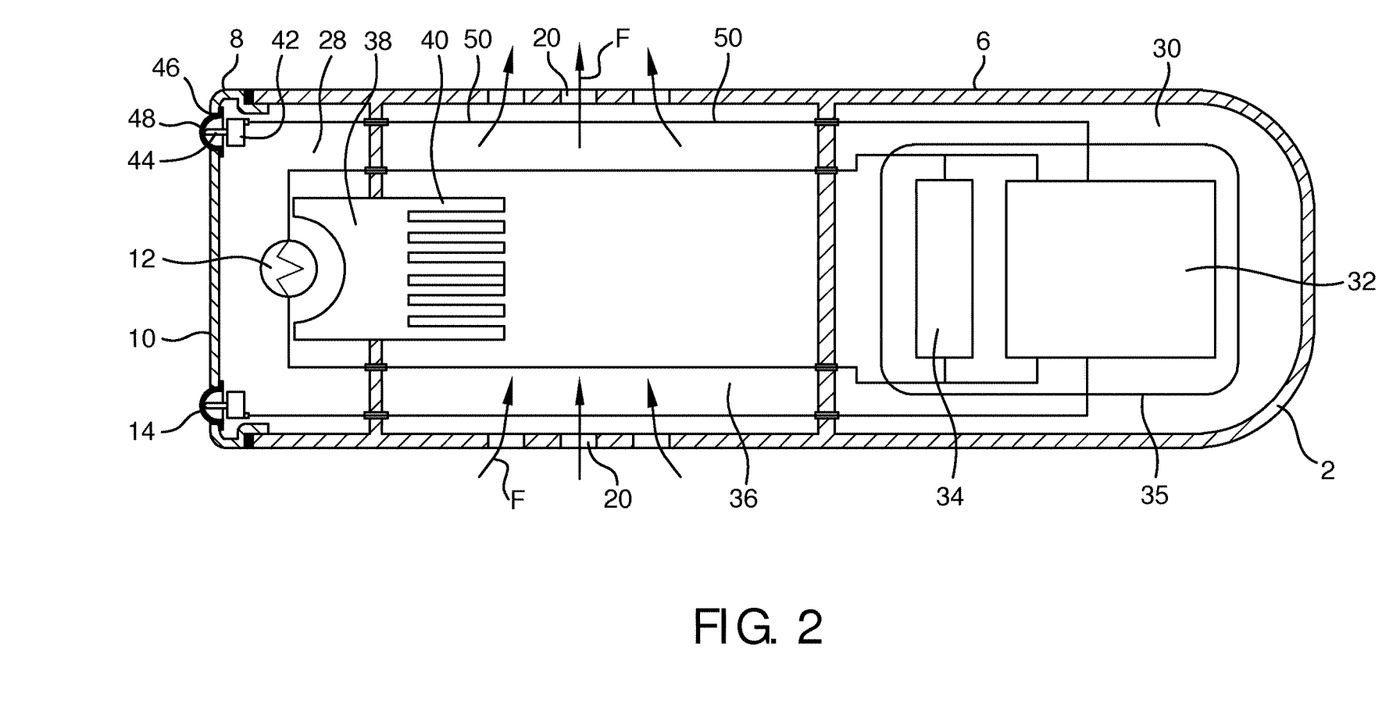
FIG. 2 shows a horizontal cross-section through the device of FIG. 1 along line II-II.

FIG. 2 shows a schematic view of the interior of the device of FIG. 1, taken along the line II-II, illustrating a number of the internal components within the watertight housing 2. Body portion 6 comprises a watertight front compartment 28 in which the flash-lamp 12 is located so as to be aligned with window 10. A watertight rear compartment 30 is formed at the rear of the body portion 6 and contains electronic components including a controller 32, a capacitor 34 and a rechargeable battery 35. Between the watertight front compartment 28 and the watertight rear compartment 30 an additional housing portion constituting a cooling compartment 36 is arranged which is in communication with the exterior of the device via the passages 20. Although the watertight front and rear compartments 28, 30 of the watertight housing 2 are depicted as separate parts in this view, it is understood that they may actually form a single watertight compartment with said front and rear compartments being interconnected above and/or below the cooling compartment 36. As can be seen, the flash-lamp 12 is mounted adjacent to a heat sink 38 which is in heat-conducting relationship with the flash-lamp 12 and which may form part of a reflector or a radiation filter. The heat sink 38 passes hermetically through a rear wall of the front compartment 28 and has cooling fins 40 which extend into the cooling compartment 36.

FIG. 2 also shows the safety detectors 14 in further detail. Each safety detector 14 comprises a mechanical microswitch 42 including an actuator rod 44 which protrudes through an opening 46 in the face plate 8. The opening 46 is hermetically sealed and covered by a watertight, flexible membrane 48. Leads 50 provide an electrical connection between the flash-lamp 12, safety detectors 14 and the electronic components in the watertight rear compartment 30. Although safety detectors 14 using mechanical microswitches are shown and described, it is understood that other forms of safety detectors could be used to perform the same function, including capacitive sensors, temperature sensors, piezo sensors and the like. Furthermore, other safety detectors for determining other variables, such as skin temperature, may also be present as required. According to the invention, the front and rear compartments 28, 30 of the watertight housing 2 are thus completely sealed against the entry of water with respect to the flash-lamp 12, controller 32, capacitor 34, battery 35, microswitches 42 and other essential electronics. It can thus be used in a wet environment including underwater, such as in a bath tub.

The IPL hair removal device as shown in FIGS. 1 and 2 may function in a similar manner to conventional IPL devices such as the Philips Lumea™ device. The controller periodically charges the capacitor 34 from the battery 35. Under actuation of the switch 16, discharge takes place through the flash-lamp 12. Discharge however can only take place when a signal is received from the mechanical microswitches 42 indicating that the face plate 8 is in full engagement with a skin surface. In this manner, accidental exposure of the eyes of a user to the light of the flash-lamp 12 is avoided. In the disclosed embodiment, six microswitches 42 are arranged around a circumference of the window 10 on the face plate 8. When the face plate 8 is pressed against a surface, such as a user's skin, the membranes 48 are depressed, causing the actuator rods 44 to actuate the microswitches 42. The capacitor is only capable of discharging when all six microswitches 42 are actuated. The light emitted passes through the window 10 and irradiates the skin. Without wishing to be bound by theory, it is understood that the light incident on the hair root is absorbed by the melanin and converted to heat, causing damage or vaporization of the hair root. During use, significant heat is produced by the flash-lamp 12 and absorbed by the heat sink 38. This heat is transmitted to the cooling fins 40 via a heat path formed by the bulk material interconnecting the heat sink 38 and the cooling fins 40. If the device is used in a dry environment, a flow of air can pass through the cooling compartment 36 via passages 20 and pass over the cooling fins 40. In the event that the device is used in a wet environment, or even underwater, water can flow through the passages 20 and provide the necessary cooling. Thus, the heat sink 38 forms an internal heat exchanger arranged inside the watertight housing 2, i.e. inside the watertight front compartment 28, and the cooling fins 40 form an external heat exchanger arranged outside of the watertight housing, i.e. arranged within the cooling compartment 36.

Figure 3:
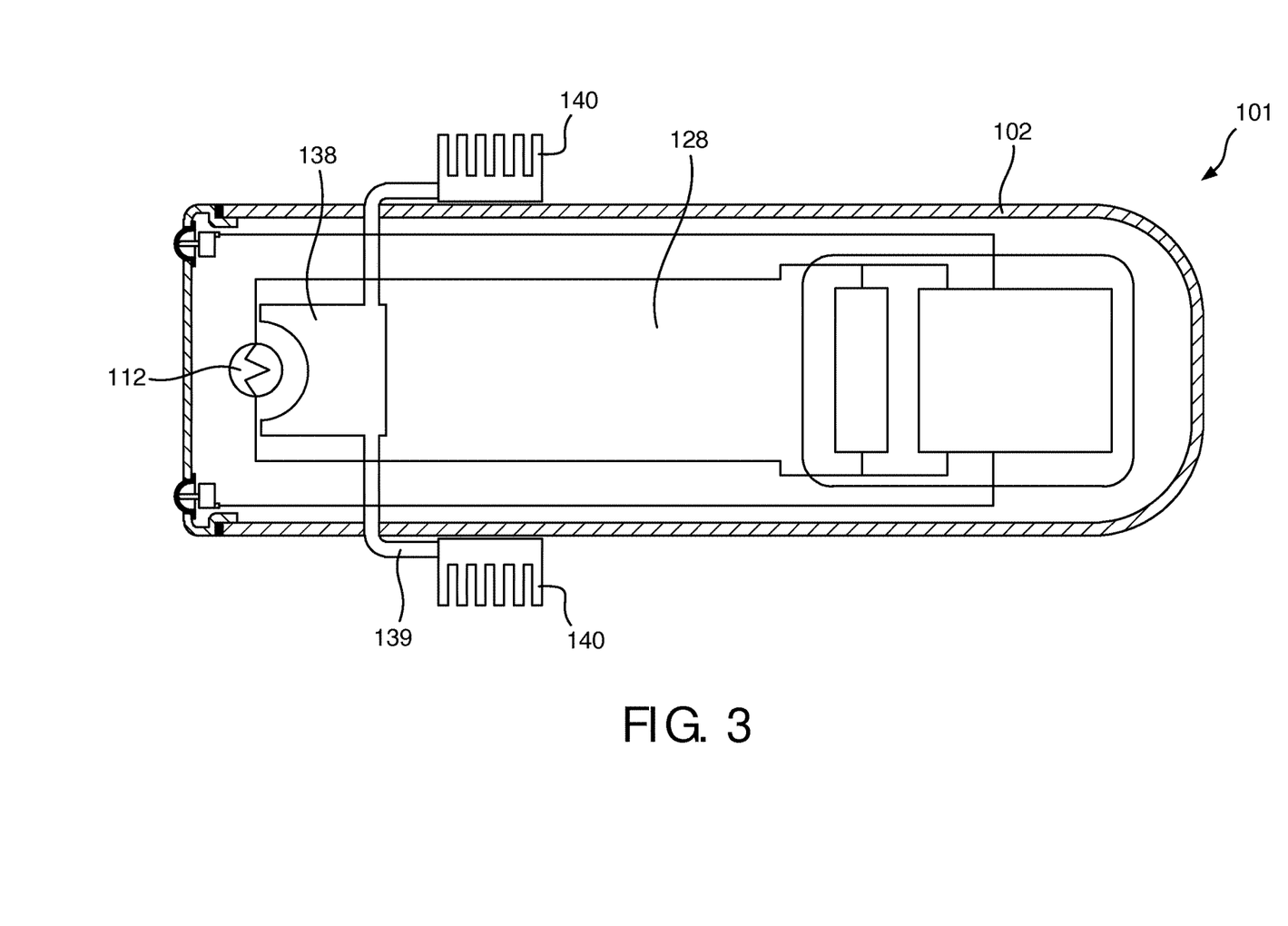
FIG. 3 shows a horizontal cross-section through a second embodiment of the invention.

A second embodiment of the invention is shown in FIG. 3, which shows a hand-held hair removal device 101 in similar cross-section to FIG. 2. In this embodiment, like elements are denoted by similar reference numerals preceded by 100.

The device 101 of FIG. 3 differs from the first embodiment in that the watertight housing 102 comprises a single watertight compartment 128 without passages to the environment. In this embodiment, a heat sink 138, which forms an internal heat exchanger and which is located inside the watertight housing 102 in heat conducting relation with the flash-lamp 112, is connected via heat pipes 139 to cooling fins 140, which form an external heat exchanger located outside of the watertight housing 102 on an external surface of the watertight housing 102. The heat pipes 139 constitute a heat path from the internal to the external heat exchanger and may be generally of a conventional type and filled with a low-pressure cooling fluid. The heat pipes 139 each pass hermetically through a wall of the watertight housing 102. The mode of operation is similar to the first embodiment except that cooling water no longer flows through passages into an additional housing portion of the device, but flows over the external surface of the watertight housing 102. Although shown exposed in this view, the skilled person will understand that the fins 140 may also be recessed in the watertight housing 102 or covered by appropriate guards to avoid contact by a user.

Figure 4:
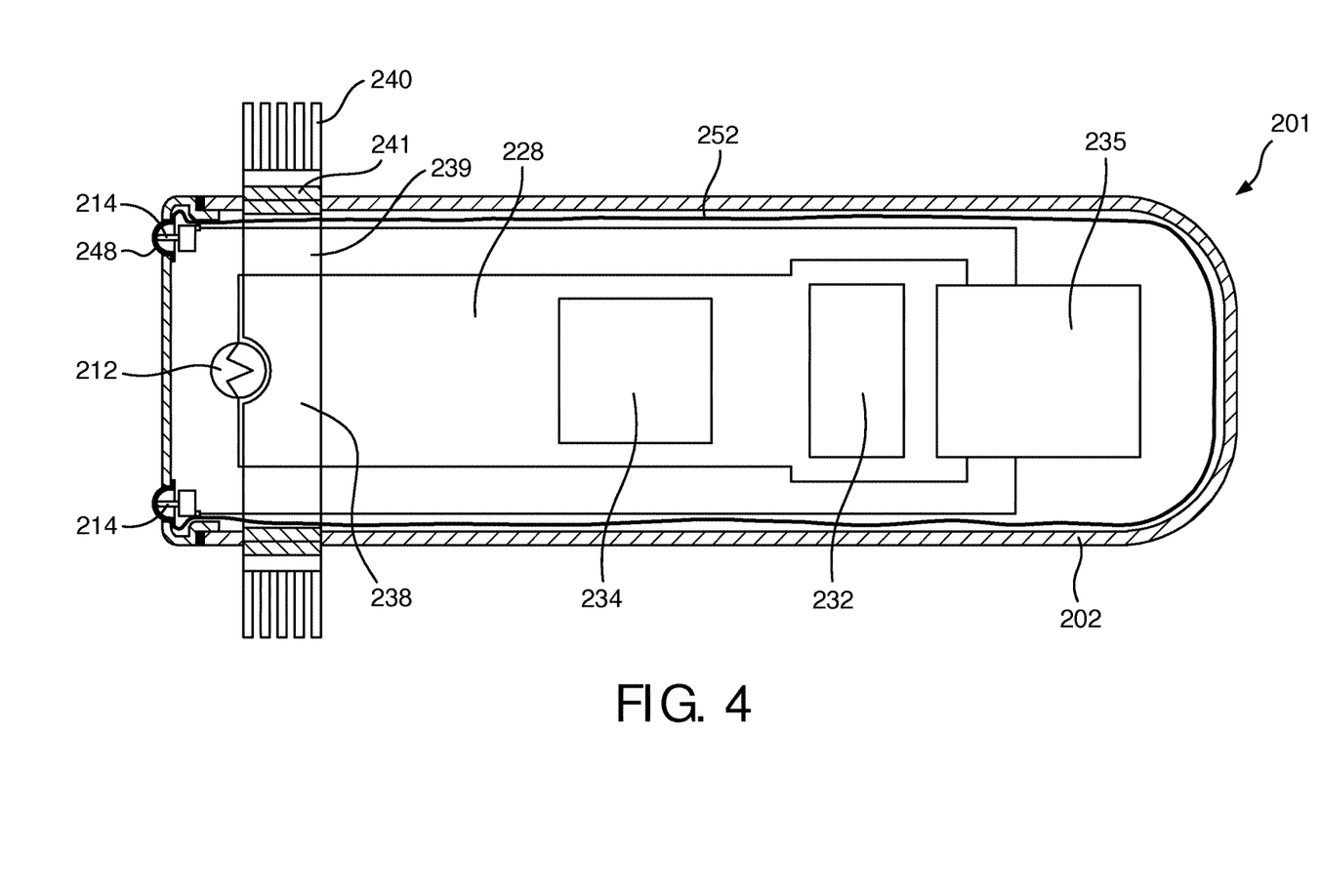
FIG. 4 shows a horizontal cross-section through a third embodiment of the invention.

A third embodiment of the invention is shown in FIG. 4, which shows a hand-held hair removal device 201, also in similar cross-section to FIG. 2. In this embodiment, like elements are denoted by similar reference numerals preceded by 200.

The device 201 of FIG. 4 differs also from the first embodiment in that the watertight housing 202 comprises a single watertight compartment 228 without passages. In this embodiment, a heat sink 238, which forms an internal heat exchanger and is located inside the watertight housing 202 in heat conducting relation with the flash-lamp 212, is connected via heat conductors 239 to cooling fins 240, which form an external heat exchanger located on an external surface of the watertight housing 202. The heat conductors 239 constitute a heat path from the internal to the external heat exchanger and pass hermetically through walls of the watertight housing 202. In order to improve heat transfer, in addition to the conductors 239 the heat path comprises Peltier elements 241 arranged between the conductors 239 and the fins 240 to increase the cooling action. The Peltier elements 241 may be driven from the battery 235 by the controller 232. In this embodiment, an impermeable flexible inner liner 252 is provided within the watertight housing 202. The flexible inner liner 252 surrounds all of the essential elements that are to be protected against the impact of water, and is integral with flexible membranes 248 covering the safety detectors 214. As a result, should the device 201 be dropped accidentally, and the watertight housing 202 be cracked, water still cannot reach the internal components.

Figure 5:
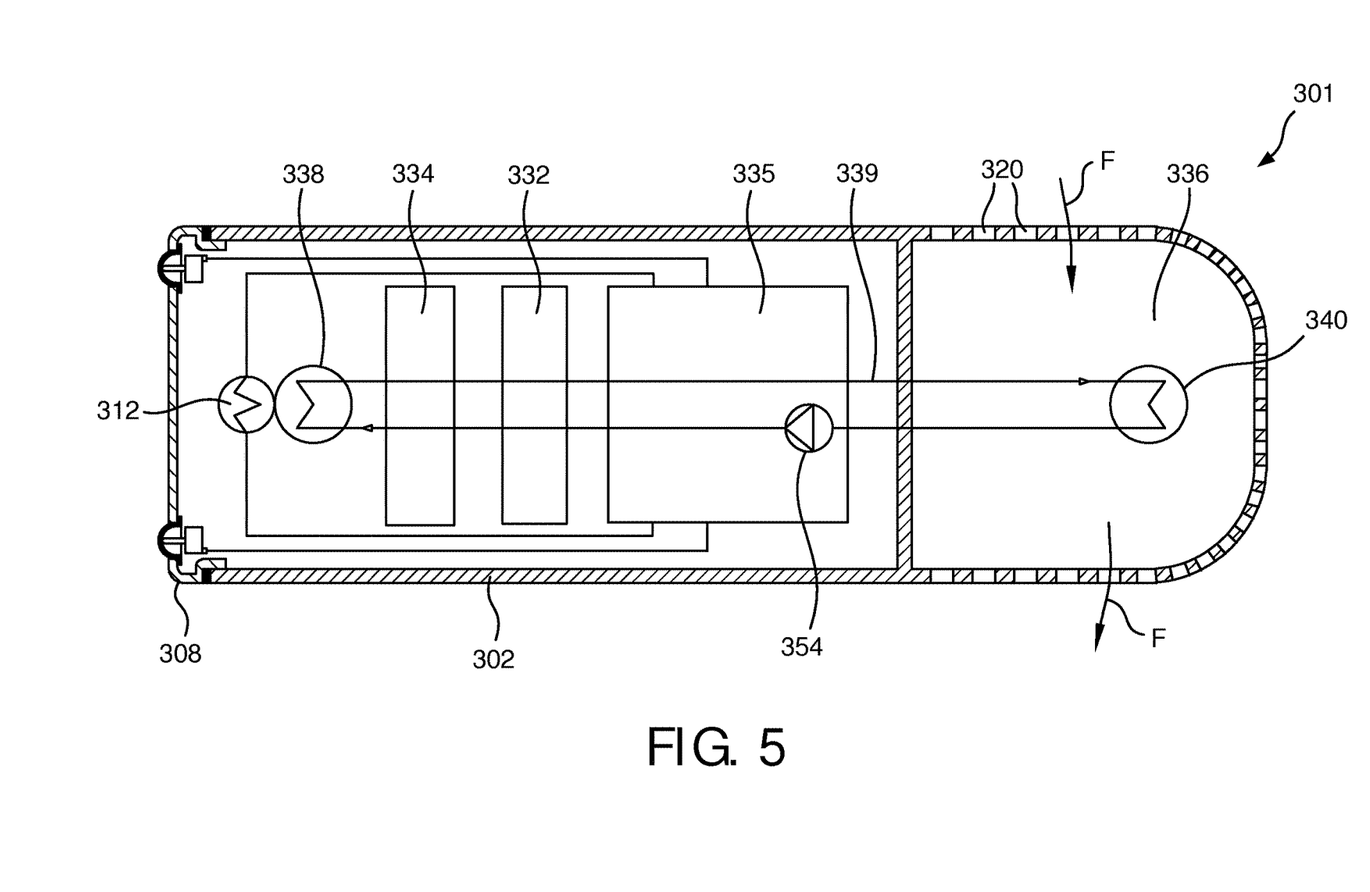
FIG. 5 shows a horizontal cross-section through a fourth embodiment of the invention.

A fourth embodiment of the invention is shown in FIG. 5, which shows a hand-held hair removal device 301, also in similar cross-section to FIG. 2. In this embodiment, like elements are denoted by similar reference numerals preceded by 300.

The device 301 of FIG. 5 differs from the previous embodiments in that a cooling compartment 336, forming an additional housing portion next to the watertight housing 302, is located at a rear side of the watertight housing 302 at a distance from the face plate 308. Heat sink 338 constitutes an internal heat exchanger in heat conducting relation with the flash-lamp 312 and is cooled by a cooling fluid circuit 339 connected with an external cooler 340, which forms an external heat exchanger outside the watertight housing 302 located within the cooling compartment 336. A pump 354 is provided in the watertight housing 302 to circulate a cooling fluid through the cooling fluid circuit 339. The cooling fluid circuit 339 constitutes a heat path from the internal heat exchanger to the external heat exchanger and passes hermetically through a rear wall of the watertight housing 302. During use, a flow F of water or air may enter the cooling compartment 336 through passages 320 to cool the external cooler 340.

Figure 6:
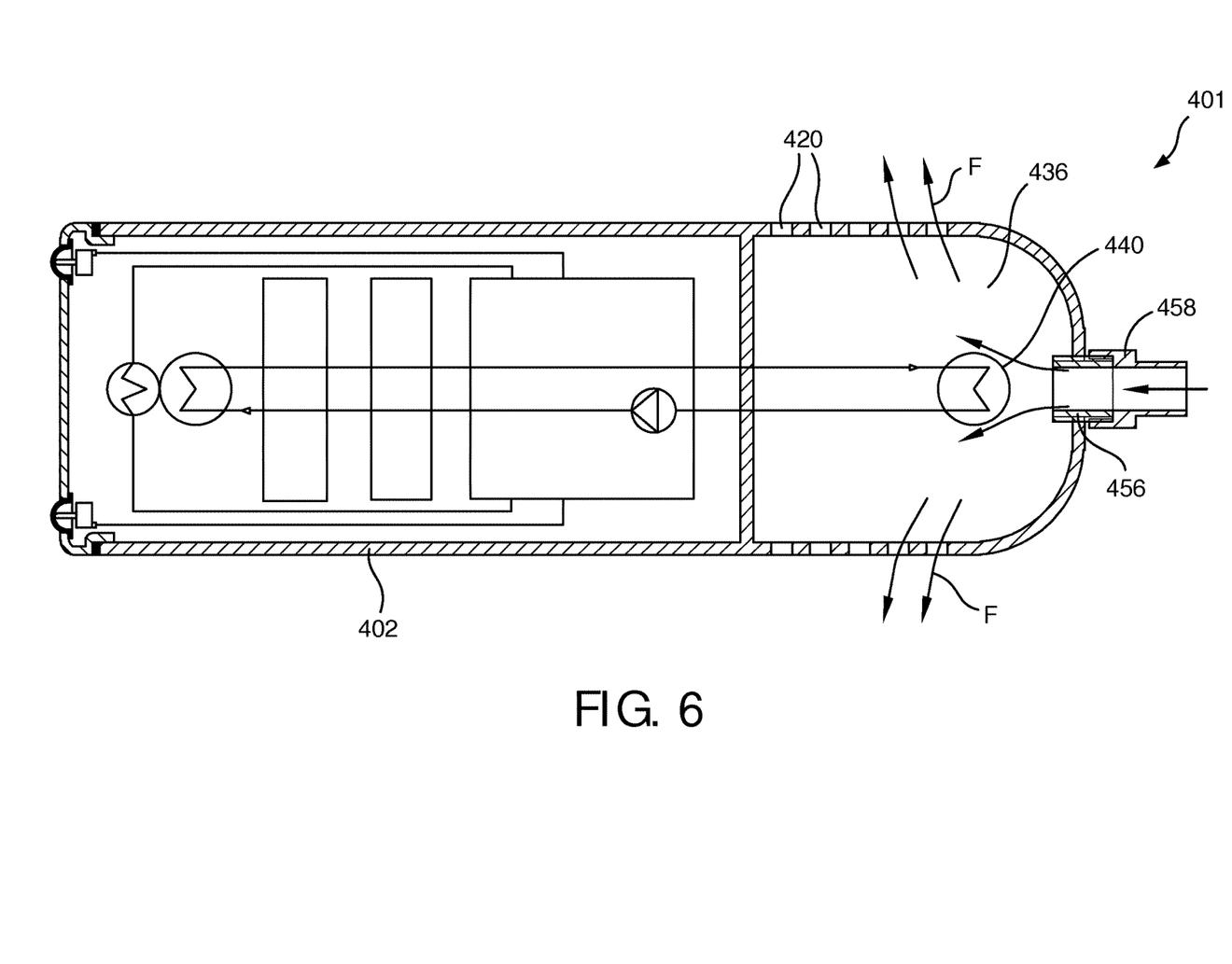
FIG. 6 shows a horizontal cross-section through a fifth embodiment of the invention.

FIG. 6 shows a device 401 according to a fifth embodiment of the invention which is an adaptation of the device of FIG. 5 for use in combination with a shower. Like reference numerals are used preceded by 400. In this embodiment, the device 401 is provided with a connector 456 for a shower hose 458 communicating with the cooling compartment 436. Cooling water from the shower hose 458 may thus be directed through the cooling compartment 436 to cool the external cooler 440.

Figure 7:
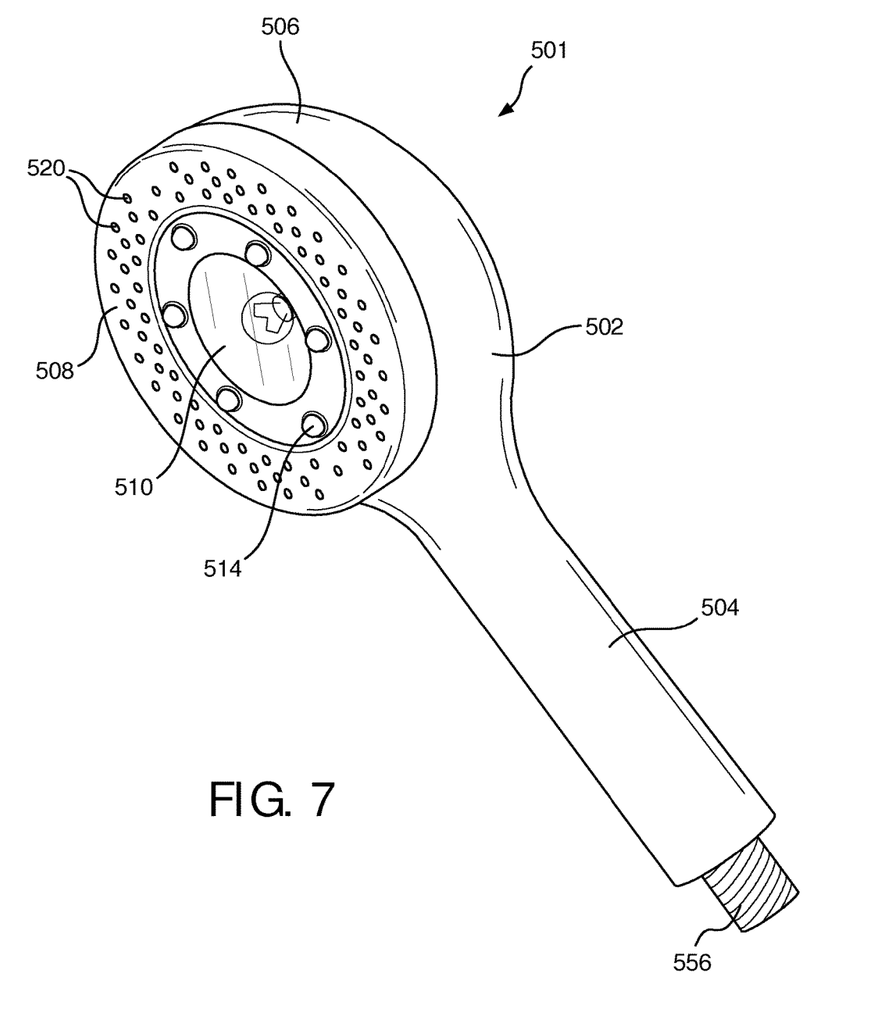
FIG. 7 shows a perspective view of a sixth embodiment of the invention.

A still further embodiment of the invention is shown in FIG. 7 in which like features to earlier embodiments are designated by like reference numerals preceded by 500.

The device 501 of FIG. 7 is in the form of a shower head and can be used during showering. It comprises a body 502 comprising a handle portion 504 and a head portion 506 including a faceplate 508. As in earlier embodiments, the faceplate 508 includes a light-output window 510 and safety detectors 514. It also includes a plurality of nozzles 520 for emitting water as is conventional for a shower head. The handle portion 504 includes a connector 556 for a shower hose.

Figure 8:
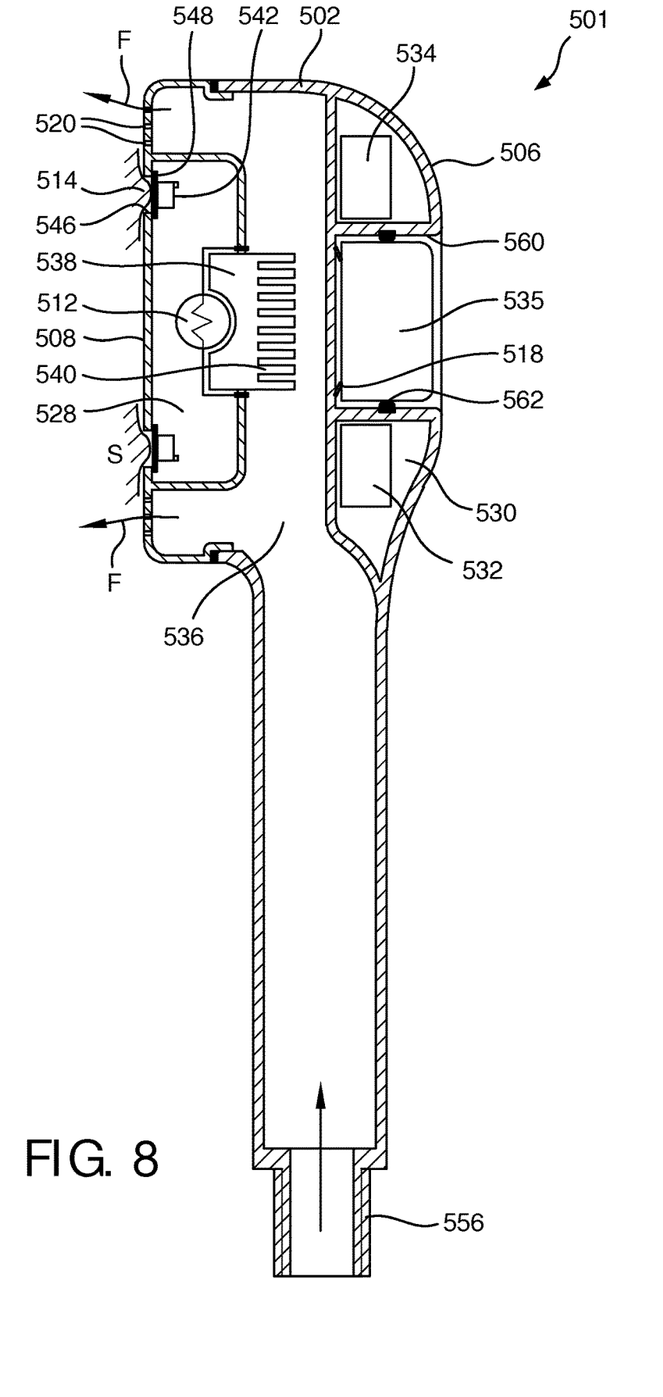
FIG. 8 shows a vertical cross-section through the device of FIG. 7.

FIG. 8 shows the device 501 of FIG. 7 in longitudinal cross-section. The inside of the main housing 502 is divided into a plurality of watertight compartments in which essential components of the device 501 are housed. An annular rear watertight compartment 530 houses a controller 532 and a capacitor 534. A circular watertight front compartment 528 houses the flash-lamp 512 and the safety detectors 514. In this embodiment, the safety detectors 514 comprise capacitive sensors 542, each being associated with and located adjacent to a blind hole 546 in the faceplate 508. Each of the blind holes 546 is open towards the user's skin and is closed at its internal end by a watertight sealing element, e.g. a membrane 548. Such capacitive sensors are otherwise conventional and operate by detection of changes in capacitance when skin domes under pressure into the blind hole 546 when the faceplate 508 is pressed against a user's skin S. Between the watertight front compartment 528 and the watertight rear compartment 530 a cooling compartment 536 is formed, which communicates with the connector 556 and the nozzles 520 and acts as a plenum chamber for the otherwise conventional shower head. A heat sink 538 forms an internal heat exchanger in heat conducting relation with the flash-lamp 512. An integral extension of the heat sink 538 passes hermetically through a rear wall of the watertight front compartment 528 and constitutes a heat path from the heat sink 538 to cooling fins 540, which form an external heat exchanger outside of the watertight front compartment 528 and which are located within the cooling compartment 536. At the rear of the head portion 506, there is provided a recess 560 for receiving a battery 535 having contacts 518. The recess 560 is provided with an O-ring seal 562 for preventing water ingress into the contacts 518. In this embodiment, the battery 535 is configured as a removable component that can be recharged separately on a charging station and inserted into the recess 560 when the user takes a shower. In this embodiment, no trigger is provided and actuation takes place automatically once the battery 535 has been engaged and the safety detectors 514 have been depressed by engagement with the skin. The skilled person will understand that other components of the device 501 may also be included in the replaceable portion inserted into the recess 560. Similarly, it will be understood that the elements contained in the front compartment 528 may also be embodied as a removable module.

Figure 9:
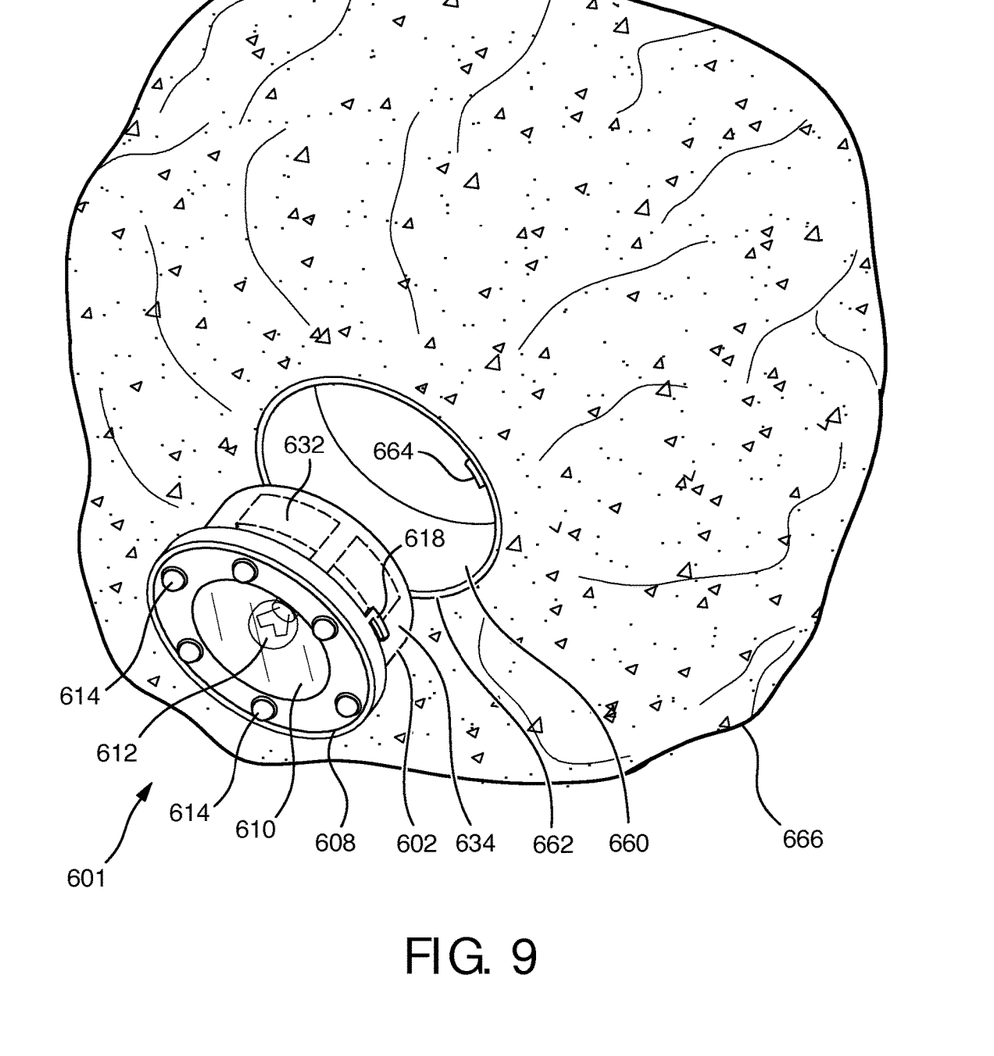
FIG. 9 shows a perspective view of a seventh embodiment of the invention.

FIG. 9 depicts a device 601 according to a seventh embodiment of the invention. The device 601 comprises a watertight housing 602 in the form of a short cylinder, having a faceplate 608, a light-output window 610, a flash-lamp 612 and safety detectors 614. The watertight housing 602 accommodates a controller 632, a capacitor 634 and other essential electronics. In this particular embodiment no battery is provided. The capacitor 634 is arranged for receiving sufficient charge for a limited number of discharges, which will depend upon the size of the capacitor and the system losses. The watertight housing 602 in this embodiment has a metal outside surface which forms an external heat exchanger which is in thermal contact with the flash-lamp 612 via an internal heat exchanger (not shown) and a heat path (not shown) to the metal outside surface according to the general principle of the present invention. In this embodiment, the metal outside surface of the watertight housing 602 is smooth, but the skilled person will understand that it could also be provided with fins or other heat dissipating structures as required. The faceplate 608 is made of plastics material and has a slightly larger diameter than the watertight housing 602. At its rear side, the faceplate is provided with L-shaped electrical contacts 618. The contacts 618 allow the device 601 to be charged on an appropriate charging station (not shown). The device 601 is intended for use in combination with a bath sponge 666, which has a recess 660 formed at one surface. The recess 660 has a rim 662 provided with bayonet connectors 664 which mechanically engage with the L-shaped contacts 618 on the watertight housing 602. In use, a user takes the device 601 from a charging station and attaches it to the sponge 666 by inserting it into the recess 660 and engaging the contacts 618 with the bayonet connectors 664. The sponge 666 is immersed in water and the device 601 is then applied to the skin in the usual way, discharge taking place automatically when the safety detectors 614 are all activated. Additional safety interlocks may be provided, e.g. a liquid (conductivity) sensor on the watertight housing 602 to ensure that activation only takes place in a wet environment.

Summarizing, the invention has been described with reference to certain embodiments discussed above. It will be recognized that these embodiments are susceptible to various modifications and alternative forms well known to those of skill in the art without departing from the spirit and scope of the invention. In particular, the hand-held hair removal device of the invention may be combined with other devices used under wet conditions, such as epilators or shavers. Accordingly, although specific embodiments have been described, these are examples only and do not limit the scope of the invention.

The invention claimed is:

1. A hand-held electromagnetic skin treatment device comprising:
   a source of electromagnetic radiation;
   an energy supply electrically coupled to the source of electromagnetic radiation;
   a controller arranged to control a supply of energy from the energy supply to the source of electromagnetic radiation, wherein responsive to the supply of energy, the source of electromagnetic radiation outputs electromagnetic radiation having a power density of at least 2 J/cm$^2$ during a pulse duration of between 1 and 100 ms;
   a housing having a watertight portion arranged to enclose the source, the energy supply and the controller for allowing use of the hand-held electromagnetic skin treatment device in a wet environment, the housing further having a cooling compartment with an interior thereof arranged in fluid communication with an exterior of the housing in the wet environment via air and water flow through passages of the cooling compartment;
   an internal heat exchanger enclosed within the watertight portion of the housing in heat conducting relation with the source, wherein the internal heat exchanger forms a part of a reflector and radiation filter;
   an external heat exchanger disposed on a wall of the watertight portion outside the watertight portion of the housing, and extending into the cooling compartment, in the wet environment; and
   a heat path from the internal heat exchanger to the external heat exchanger that passes hermetically through the wall of the watertight portion of the housing, wherein together the (i) internal heat exchanger, (ii) heat path and (iii) external heat exchanger that extends into the cooling compartment jointly provide cooling of the source of electromagnetic radiation arranged in the watertight portion of the housing.

2. The device according to claim 1, wherein the internal heat exchanger comprises a heat sink and the external heat exchanger comprises cooling fins.

3. The device according to claim 1, wherein the heat path comprises a cooling fluid circuit at least partially within the watertight housing.

4. The device according to claim 2, wherein the heat path comprises one or more heat pipes that connect the heat sink to the cooling fins.

5. The device according to claim 2, wherein the heat path comprises at least one Peltier element that connects the heat sink to the cooling fins.

6. The device according to claim 1, wherein the device comprises an additional housing portion with passages through which water from an environment may flow without entering an interior of the watertight portion of the housing, and wherein the external heat exchanger is located at least partially in the additional housing portion.

7. The device according to claim 1, wherein the housing forms part of a shower head connectable to a supply of water, and wherein the external heat exchanger is located within an interior of the shower head such that the water supplied can flow over the external heat exchanger.

8. The device according to claim 1, wherein the device comprises part of a washing glove or scrubbing sponge, and wherein the external heat exchanger is located within an interior of the glove or sponge such that it is contacted by water but is not in contact with a hand of the user during normal use.

9. The device according to claim 1, wherein the watertight portion of the housing comprises a faceplate for engaging a user's skin during use, the faceplate having a window allowing irradiation of the skin with electromagnetic radiation from the source through the window.

10. The device according to claim 9, wherein the device further comprises safety detectors disposed around a circumference of the window, the safety detectors being watertight.

11. The device according to claim 10, wherein the safety detectors comprise mechanical microswitches having actuator rods protruding through openings in the faceplate, said openings being covered by watertight flexible membranes.

12. The device according to claim 10, wherein the safety detectors comprise capacitive sensors, each sensor being associated with a blind hole in the face plate and being arranged to measure a change in capacitance due to skin doming into the blind hole on application of pressure, wherein a watertight sealing element is present between each capacitive sensor and the associated blind hole.

13. The device according to claim 1, wherein the source of electromagnetic radiation comprises a flash-lamp and the device is an intense pulsed light (IPL) device.

14. The device according to claim 1, wherein the watertight portion of the housing comprises one or more impermeable flexible inner liners hermetically enclosing at least the source, the energy supply and the controller.

* * * * *